(12) United States Patent
Moroney

(10) Patent No.: US 11,357,876 B2
(45) Date of Patent: Jun. 14, 2022

(54) COMPOSITIONS AND METHODS OF MAKING AND USING THE SAME

(71) Applicant: Eastern Technologies, Inc., Ashford, AL (US)

(72) Inventor: Mark Steven Moroney, Cave Creek, AZ (US)

(*) Notice: Subject to any disclaimer, the term of this patent is extended or adjusted under 35 U.S.C. 154(b) by 0 days.

(21) Appl. No.: 16/338,005

(22) PCT Filed: Sep. 29, 2017

(86) PCT No.: PCT/US2017/054238
§ 371 (c)(1),
(2) Date: Mar. 29, 2019

(87) PCT Pub. No.: WO2018/064445
PCT Pub. Date: Apr. 5, 2018

(65) Prior Publication Data
US 2019/0231911 A1  Aug. 1, 2019

Related U.S. Application Data

(60) Provisional application No. 62/402,397, filed on Sep. 30, 2016.

(51) Int. Cl.
A61L 2/00     (2006.01)
A61L 2/18     (2006.01)
A61L 2/22     (2006.01)
A61L 15/18    (2006.01)
A61L 17/00    (2006.01)
A61L 31/08    (2006.01)
A61L 29/10    (2006.01)
A61L 27/30    (2006.01)
A61L 26/00    (2006.01)
A61L 15/44    (2006.01)
A61L 15/46    (2006.01)

(52) U.S. Cl.
CPC ............. *A61L 2/0088* (2013.01); *A61L 2/18* (2013.01); *A61L 2/22* (2013.01); *A61L 15/18* (2013.01); *A61L 17/005* (2013.01); *A61L 27/306* (2013.01); *A61L 29/106* (2013.01); *A61L 31/088* (2013.01); *A61L 2/00* (2013.01); *A61L 15/44* (2013.01); *A61L 15/46* (2013.01); *A61L 26/0004* (2013.01); *A61L 2300/106* (2013.01); *A61L 2300/406* (2013.01); *A61L 2420/02* (2013.01)

(58) Field of Classification Search
None
See application file for complete search history.

(56) References Cited

U.S. PATENT DOCUMENTS

| 3,326,747 A * | 6/1967 | Ryan ................. | C02F 1/766 424/667 |
| 2005/0142157 A1 | 6/2005 | Alimi | |
| 2011/0059028 A1* | 3/2011 | Ponitz ................. | A61K 33/04 424/49 |
| 2013/0028787 A1* | 1/2013 | Takeuchi ............. | A01N 59/00 422/28 |

FOREIGN PATENT DOCUMENTS

| CN | 103 548 900 A | 2/2014 | |
| DE | 10 2011 055182 | 5/2013 | |
| EP | 2387990 | 11/2011 | |
| EP | 2559339 A1 | 2/2013 | |
| JP | H08155459 A | 6/1996 | |
| JP | 2004346162 A | 12/2004 | |
| WO | 2005065383 | 7/2005 | |
| WO | WO-2005065383 A2 * | 7/2005 | ........... A61K 9/0014 |
| WO | 2008089268 A2 | 7/2008 | |
| WO | 2008140200 | 11/2008 | |
| WO | 2009010203 A1 | 1/2009 | |
| WO | 2011014809 | 2/2011 | |
| WO | 2013134327 A1 | 9/2013 | |

OTHER PUBLICATIONS

PCT/US2017/054238 International Search Report, dated Dec. 20, 2017.

* cited by examiner

*Primary Examiner* — Susan T Tran
*Assistant Examiner* — William Craigo
(74) *Attorney, Agent, or Firm* — Withers & Keys, LLC

(57) ABSTRACT

Compositions that are suitable for use as a disinfectant are disclosed. Methods of making and using compositions that are suitable for use as a disinfectant are also disclosed.

3 Claims, No Drawings

COMPOSITIONS AND METHODS OF MAKING AND USING THE SAME

This application is being filed as the national stage patent application of PCT International Patent Application No. PCT/US2017/054238, filed on 29 Sep. 2017, which claims priority to U.S. Provisional Patent Application Ser. No. 62/402,397 filed on 30 Sep. 2016, the contents of both of which are (i) entitled "COMPOSITIONS AND METHODS OF MAKING AND USING THE SAME," and (ii) incorporated herein by reference in its entirety.

FIELD OF THE INVENTION

The present invention is directed to compositions suitable for use as a disinfectant. The present invention is further directed to methods of making and using compositions to disinfect an area.

BACKGROUND

Efforts continue to further develop compositions that are suitable for use as a disinfectant.

SUMMARY

The present invention addresses some of the difficulties and problems discussed above by the discovery of new compositions that are suitable for use as a disinfectant.

Accordingly, the present invention is directed to compositions that are suitable for use as a disinfectant. In one exemplary embodiment, the composition of the present invention comprises: electrolyzed water containing one or more solubilized salts and having an oxidation reduction potential (ORP) value ranging from about +100 mv to about +1600 mv; and alum or ionic components resulting from solubilized alum within said electrolyzed water, wherein said composition is useful as a disinfectant. In another exemplary embodiment, the composition of the present invention comprises: electrolyzed water containing one or more solubilized salts and having an oxidation reduction potential (ORP) value ranging from about +100 mv to about +1600 mv; potassium iodine; and alum or ionic components resulting from solubilized alum within said electrolyzed water, wherein said composition is useful as a disinfectant and has a pH value ranging between about 2.5 and about 4.0.

The present invention further relates to surfaces and devices coated with a composition comprising: electrolyzed water containing one or more solubilized salts and having an oxidation reduction potential (ORP) value ranging from about +100 mv to about +1600 mv; and alum or ionic components resulting from solubilized alum within said electrolyzed water. The surface may be on an animate or inanimate object. The device may be, for example, a pharmaceutically acceptable device selected from the group consisting of: bandages, surgical dressings, gauzes, adhesive strips, surgical staples, clips, hemostats, intrauterine devices, sutures, trocars, catheters, tubes, implants, and any combination thereof.

In some desired embodiments, the surfaces and/or devices are coated with a composition comprising: electrolyzed water containing one or more solubilized salts and having an oxidation reduction potential (ORP) value ranging from about +100 mv to about +1600 mv; potassium iodine; and alum or ionic components resulting from solubilized alum within said electrolyzed water, wherein said composition is useful as a disinfectant and has a pH value ranging between about 2.5 and about 4.0. In some embodiments, at least a portion of a surface of a pharmaceutically acceptable device selected from the group consisting of: bandages, surgical dressings, gauzes, adhesive strips, surgical staples, clips, hemostats, intrauterine devices, sutures, trocars, catheters, tubes, implants, and any combination thereof is coated with a composition comprising: electrolyzed water containing one or more solubilized salts and having an oxidation reduction potential (ORP) value ranging from about +100 mv to about +1600 mv; potassium iodine; and alum or ionic components resulting from solubilized alum within said electrolyzed water, wherein said composition is useful as a disinfectant and has a pH value ranging between about 2.5 and about 4.0.

The present invention even further relates to methods of making compositions that are suitable for use as a disinfectant. In one exemplary embodiment, the method of making a composition comprises: adding one or more one or more solubilized salts to deionized or purified water to form a salt solution; subjecting the salt solution to an oxidizing or reducing step to alter an oxidation reduction potential (ORP) value of the salt solution and form an ionized solution; and adding alum to the ionized solution, wherein the composition has an ORP value ranging from about +100 mv to about +1600 mv. In some embodiments, the method of making the composition further comprises: also adding potassium iodine to the ionized solution, and forming a final solution having a pH value ranging between about 2.5 and about 4.0.

The present invention even further relates to methods of using compositions. In one exemplary embodiment, the method of using a composition comprises a method of treating a surface, wherein the method comprises: applying a composition onto a surface portion of the surface, the composition comprising: electrolyzed water containing one or more solubilized salts and having an oxidation reduction potential (ORP) value ranging from about +100 mv to about +1600 mv; and alum or ionic components resulting from solubilized alum within said electrolyzed water. In another exemplary embodiment, the method of using a composition comprises a method of treating a surface, wherein the method comprises: applying a composition onto a surface portion of the surface, the composition comprising: electrolyzed water containing one or more solubilized salts and having an oxidation reduction potential (ORP) value ranging from about +100 mv to about +1600 mv; potassium iodine; and alum or ionic components resulting from solubilized alum within said electrolyzed water, wherein said composition is useful as a disinfectant and has a pH value ranging between about 2.5 and about 4.0.

These and other features and advantages of the present invention will become apparent after a review of the following detailed description of the disclosed embodiments and the appended claims.

DETAILED DESCRIPTION

To promote an understanding of the principles of the present invention, descriptions of specific embodiments of the invention follow and specific language is used to describe the specific embodiments. It will nevertheless be understood that no limitation of the scope of the invention is intended by the use of specific language. Alterations, further modifications, and such further applications of the principles of the present invention discussed are contemplated as would normally occur to one ordinarily skilled in the art to which the invention pertains.

The present invention is directed to compositions that are suitable for use as a disinfectant. The present invention is further directed to methods of compositions that are suitable for use as a disinfectant. The present invention is even further directed to methods of using compositions that are suitable for use as a disinfectant.

The compositions of the present invention are further described in the following embodiments.

Other Embodiments

Compositions

1. A composition comprising: electrolyzed water containing one or more solubilized salts and having an oxidation reduction potential (ORP) value ranging from about +100 mv to about +1600 mv (or any ORP value between about +100 and about +1600, including endpoints +100 mv and +1600 mv, in increments of 1.0 mv, e.g., 450 mv, or any range of ORP values between about +100 and about +1600, including endpoints +100 mv and +1600 my, in increments of 1.0 mv, e.g., from about 425 mv to about 1150 mv); and alum or ionic components resulting from dissociated alum within said electrolyzed water, wherein said composition is useful as a disinfectant.
2. The composition of embodiment 1, wherein said one or more solubilized salts comprise sodium chloride, himalayan salt, potassium chloride, or any combination thereof
3. The composition of embodiment 1 or 2, wherein said one or more solubilized salts comprise sodium chloride.
4. The composition of any one of embodiments 1 to 3, wherein the alum comprises one or more compounds having the general structure

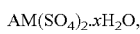
$$AM(SO_4)_2 \cdot xH_2O,$$

wherein A represents a monovalent cation, M represents a trivalent metal ion, and x represents an integer ranging from 6 to 24 (or any integer between about 6 and about 24, including endpoints 6 and 24, in increments of 1.0, e.g., 12, or any range of integer between about 6 and about 24, including endpoints 6 and 24, in increments of 1.0, e.g., from about 12 my to about 18).
5. The composition of embodiment 4, wherein A is a potassium, sodium or ammonium cation.
6. The composition of embodiment 4 or 5, wherein M is aluminum or chromium.
7. The composition of any one of embodiments 4 to 6, wherein x is 12 or 24.
8. The composition of any one of embodiments 1 to 3, wherein the alum comprises one or more compounds having the general structure

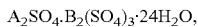
$$A_2SO_4 \cdot B_2(SO_4)_3 \cdot 24H_2O,$$

wherein A represents a monovalent cation comprising sodium, potassium, rubidium, cesium, or thallium(I), or a monovalent compound cation such as ammonium ($NH_4^+$), methylammonium ($CH_3NH_3^+$), hydroxylammonium ($HONH_3^+$) or hydrazinium ($N_2H_5^+$); B is a trivalent metal ion comprising aluminum, chromium, titanium, manganese, vanadium, iron(III), cobalt(III), gallium, molybdenum, indium, ruthenium, rhodium, or iridium.
9. The composition of any one of embodiments 1 to 7, wherein the alum comprises potassium alum.
10. The composition of any one of embodiments 1 to 7, wherein the alum comprises soda alum.
11. The composition of any one of embodiments 1 to 7, wherein the alum comprises ammonium alum.
12. The composition of any one of embodiments 1 to 11, wherein the alum is present in an amount of greater than 0 weight percent (wt %) to about 3.0 wt %, based on a total weight of the composition (or any wt % between about 0.001 wt % and about 3.0 wt %, including endpoints 0.001 wt % and 3.0 wt %, in increments of 0.001 wt %, e.g., 0.015 wt %, or any range of wt % between about 0.001 wt % and 3.0 wt %, including endpoints 0.001 wt % and 3.0 wt %, in increments of 0.001 wt %, e.g., from about 0.001 wt % to about 0.03 wt %).
13. The composition of any one of embodiments 1 to 12, wherein the alum is present in an amount of from about 0.001 wt % to about 0.003 wt %.
14. The composition of any one of embodiments 1 to 11, wherein said one or more solubilized salts are present in an amount of greater than 0 wt % to about 30.0 wt %, based on a total weight of the composition (or any wt % between about 0.01 wt % and about 30.0 wt %, including endpoints 0.01 wt % and 30.0 wt %, in increments of 0.01 wt %, e.g., 20.1 wt %, or any range of wt % between about 0.01 wt % and 30.0 wt %, including endpoints 0.01 wt % and 30.0 wt %, in increments of 0.01 wt %, e.g., from about 26.5 wt % to about 30.6 wt %).
15. The composition of any one of embodiments 1 to 14, wherein said composition further comprises an available free chlorine (AFC) value of from 0 ppm to about 250 ppm (or any AFC value between 0.0 ppm and about 250 ppm, including endpoints 0.0 ppm and 250 ppm, in increments of 0.1 ppm, e.g., 4.1 ppm, or any range of AFC values between 0.0 ppm and about 250 ppm, including endpoints 0.0 ppm and 250 ppm, in increments of 0.1 ppm, e.g., from about 20.1 ppm to about 35.7 ppm).
16. The composition of any one of embodiments 1 to 15, wherein said composition further comprises an available free chlorine (AFC) value of from greater than 0 ppm to about 100 ppm.
17. The composition of any one of embodiments 1 to 16, wherein said composition has a pH of from about 1.5 to about 7.0 (or any pH between about 1.5 and about 7.0, including endpoints 1.5 and 7.0, in increments of 0.1, e.g., 2.7, or any range of pH between about 1.5 to about 7.0, including endpoints 1.5 and 7.0, in increments of 0.1, e.g., from about 2.4 to about 6.1 or from about 2.5 to about 4.0).
18. The composition of any one of embodiments 1 to 17, wherein said composition has a pH of from about 2.0 to about 6.0. In some exemplary embodiments, the composition of the present invention has a pH value ranging between about 2.5 and about 4.0.
19. The composition of any one of embodiments 1 to 18, wherein the electrolyzed water has an oxidation reduction potential (ORP) value ranging from about +300 mv to about +1300 mv.
20. The composition of any one of embodiments 1 to 19, wherein the electrolyzed water has an oxidation reduction potential (ORP) value ranging from about +500 mv to about +1150 mv.
21. The composition of any one of embodiments 1 to 20, wherein the composition further comprises one or more additional components, said one or more additional components comprising one or more minerals, one or more vitamins, one or more medicines, or any combination thereof
22. The composition of any one of embodiments 1 to 21, wherein the composition further comprises one or more medicines comprising potassium iodide.

23. The composition of any one of embodiments 1 to 22, wherein the composition further comprises one or more medicines comprising boric acid.
24. The composition of any one of embodiments 1 to 23, wherein the composition further comprises one or more medicines comprising iodoform.
25. The composition of any one of embodiments 21 to 24, wherein each of the one or more additional components is present in an amount of greater than 0 wt % to about 3.0 wt %, based on a total weight of the composition (or any wt % between about 0.001 wt % and about 3.0 wt %, including endpoints 0.001 wt % and 3.0 wt %, in increments of 0.001 wt %, e.g., 0.011 wt %, or any range of wt % between about 0.001 wt % and 3.0 wt %, including endpoints 0.001 wt % and 3.0 wt %, in increments of 0.001 wt %, e.g., from about 0.001 wt % to about 0.013 wt %). For example, in some embodiments, potassium iodide is present in an amount of from about 0.01 to about 0.10 wt %, based on a total weight of the composition.
26. The composition of any one of embodiments 1 to 25, wherein the composition is in the form of a liquid, gel, cream, or foam.
27. The composition of any one of embodiments 1 to 25, wherein the composition is stable for at least 6 months. By "stable" it is meant that the composition is still effective and retains disinfection properties for use after 6 months when stored at a temperature of up to about 100° F.
28. The composition of any one of embodiments 1 to 27, wherein the composition is stable for at least 1 year.

Surface Embodiments

29. A surface at least partially covered with said composition of any one of embodiments 1 to 28.
30. The surface of embodiment 29, wherein said surface comprises an inanimate or animate object.
31. The surface of embodiment 29 or 30, wherein said surface comprises an animate object.
32. The surface of any one of embodiments 29 to 31, wherein said surface comprises a wound site, a tissue laceration, or an incision site.
33. The surface of embodiment 29 or 30, wherein said surface comprises a surface portion of a pharmaceutically acceptable device selected from the group consisting of: bandages, surgical dressings, gauzes, adhesive strips, surgical staples, clips, hemostats, intrauterine devices, sutures, trocars, catheters, tubes, implants, and any combination thereof.

Device Embodiments

34. A pharmaceutically acceptable device comprising a substrate having a surface portion, said surface portion being treated with the composition of any one of embodiments 1 to 28.
35. The device of embodiment 34, wherein the substrate comprises a substrate selected from the group consisting of: bandages, surgical dressings, gauzes, adhesive strips, surgical staples, clips, hemostats, intrauterine devices, sutures, trocars, catheters, tubes, implants, and any combination thereof.

Various Embodiments

36. The composition of any one of embodiments 1 to 28, the surface of any one of embodiments 29 to 33, or the device of embodiment 34 or 35, wherein the composition, the surface, or the device provides effective antimicrobial properties to a coating, or a treated surface, or a substrate.
37. The composition, surface, or device of embodiment 36, wherein the effective antimicrobial properties comprises effectiveness against one or more of: methicillin-resistant *Staphylococcus aureus* (MRSA) infection, *Escherichia coli* (*E. coli*), *Pseudomonas aeruginosa* (*P. aeruginosa*), *Salmonella enterica* (*S. enterica*), and *Candida albicans* (*C. albicans*), *Listeria monocytogenes* 10403s wild type, catalase-deficient mutant *L. monocytogenes* LM1370, *Aspergillus niger* (spores), *Penecillium oblatum* (spores), and *Lactobacillus*.

Methods of Using Compositions

38. A method of treating a surface, said method comprising: applying the composition of any one of embodiments 1 to 28 onto a surface portion of the surface.
39. The method of embodiment 38, wherein the surface comprises the surface of any one of embodiments 29 to 33.
40. The method of embodiment 38 or 39, wherein the surface comprises an open wound on an animate object.
41. The method of embodiment 40, wherein the composition is applied for a period of time to cause closure of the open wound.
42. The method of embodiment 38 or 39, wherein the surface comprises a closed wound.
43. The method of embodiment 38 or 39, wherein the surface comprises a tissue laceration.
44. The method of embodiment 38 or 39, wherein the surface comprises an incision site.
45. The method of any one of embodiments 38 to 44, wherein said applying step comprises: applying the composition onto the surface using at least four separate applications.
46. The method of any one of embodiments 38 to 45, wherein said applying step comprises: applying the composition onto the surface over a period ranging from about 1 minute (min) to about 7 days.
47. The method of any one of embodiments 38 to 46, wherein said applying step comprises: applying the composition onto the surface over a period of at least 4 days.
48. The method of any one of embodiments 38 to 46, wherein said applying step comprises: spraying the composition.
49. The method of any one of embodiments 38 to 48, wherein said applying step comprises: spraying the composition via a spray bottle with extension tube, handheld wand, and self-contained manual pump mechanism.
50. The method of any one of embodiments 38 to 49, wherein the surface comprises a surface portion of a vertebrate.
51. The method of embodiment 50, wherein the vertebrate is mammal.
52. The method of embodiment 50 or 51, wherein the vertebrate is a non-human mammal.
53. The method of any one of embodiments 50 to 52, wherein the vertebrate is a horse, a pet (e.g., a dog, a cat, a bird, or any other companion pet.
54. The method of any one of embodiments 38 to 53, wherein the composition is used in a veterinary clinic or office or setting.
55. The method of embodiment 50 or 51, wherein the vertebrate is a human.

56. The method of embodiment 50 or 51 or 55, wherein the vertebrate is a newborn and the surface is a navel of the newborn.
57. The method of any one of embodiments 38 to 56, wherein the surface is not a burn.
58. The method of any one of embodiments 38 to 57, wherein the surface further comprises spores, mold, or any other bacteria.
59. The method of any one of embodiments 38 to 58, wherein the surface comprises a chronic infection.
60. The method of any one of embodiments 38, 39, 45 to 49, 54, or 57 to 59, wherein the surface comprises a surface portion of a device selected from the group consisting of bandages, surgical dressings, gauzes, adhesive strips, surgical staples, clips, hemostats, intrauterine devices, sutures, trocars, catheters, tubes, implants, and any combination thereof.

Methods of Making Compositions

61. A method of making the composition of any one of embodiments 1 to 28, said method comprising: adding one or more one or more solubilized salts to deionized or purified water to form a salt solution; subjecting the salt solution to an oxidizing or reducing step to alter an oxidation reduction potential (ORP) value of the salt solution and form an ionized solution; and adding alum to the ionized solution, wherein the composition has an ORP value ranging from about +100 mv to about +1600 mv.
62. The method of embodiment 61, wherein the one or more solubilized salts comprise sodium chloride, himalayan salt, potassium chloride, or any combination thereof
63. The method of embodiment 61 or 62, wherein the one or more solubilized salts comprise sodium chloride.
64. The method of any one of embodiments 61 to 63, wherein the alum comprises one or more compounds having the general structure

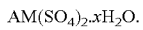
AM(SO$_4$)$_2$·xH$_2$O.

wherein A represents a monovalent cation, M represents a trivalent metal ion, and x represents an integer ranging from 6 to 24 (or any integer between about 6 and about 24, including endpoints 6 and 24, in increments of 1.0, e.g., 12, or any range of integer between about 6 and about 24, including endpoints 6 and 24, in increments of 1.0, e.g., from about 12 my to about 18).
65. The method of embodiment 64, wherein A is a potassium, sodium or ammonium cation.
66. The method of embodiment 64 or 65, wherein M is aluminum or chromium.
67. The method of any one of embodiments 64 to 66, wherein x is 12 or 24.
68. The method of embodiment 61 to 63, wherein the alum comprises one or more compounds having the general structure

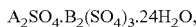
A$_2$SO$_4$·B$_2$(SO$_4$)$_3$·24H$_2$O, wherein A represents a monovalent cation comprising sodium, potassium, rubidium, cesium, or thallium(I), or a monovalent compound cation such as ammonium (NH$_4^+$), methylammonium (CH$_3$NH$_3^+$), hydroxylammonium (HONH$_3^+$) or hydrazinium (N$_2$H$_5^+$); B is a trivalent metal ion comprising aluminum, chromium, titanium, manganese, vanadium, iron(III), cobalt(III), gallium, molybdenum, indium, ruthenium, rhodium, or iridium.
69. The method of any one of embodiments 61 to 67, wherein the alum comprises potassium alum.
70. The method of any one of embodiments 61 to 67, wherein the alum comprises soda alum.
71. The method of any one of embodiments 61 to 67, wherein the alum comprises ammonium alum.
72. The method of any one of embodiments 61 to 71, wherein the alum is present in an amount of greater than 0 weight percent (wt %) to about 3.0 wt %, based on a total weight of the composition (or any wt % between about 0.001 wt % and about 3.0 wt %, including endpoints 0.001 wt % and 3.0 wt %, in increments of 0.001 wt %, e.g., 0.011 wt %, or any range of wt % between about 0.001 wt % and 3.0 wt %, including endpoints 0.001 wt % and 3.0 wt %, in increments of 0.001 wt %, e.g., from about 0.001 wt % to about 0.013 wt %).
73. The method of any one of embodiments 61 to 72, wherein the alum is present in an amount of from about 0.001 wt % to about 0.03 wt %.
74. The method of any one of embodiments 61 to 71, wherein the one or more solubilized salts are present in an amount of greater than 0 wt % to about 30.0 wt %, based on a total weight of the composition (or any wt % between about 0.01 wt % and about 30.0 wt %, including endpoints 0.01 wt % and 30.0 wt %, in increments of 0.01 wt %, e.g., 20.1 wt %, or any range of wt % between about 0.01 wt % and 30.0 wt %, including endpoints 0.01 wt % and 30.0 wt %, in increments of 0.01 wt %, e.g., from about 26.5 wt % to about 30.6 wt %).
75. The method of any one of embodiments 61 to 74, wherein the composition further comprises an available free chlorine (AFC) value of from 0 ppm to about 250 ppm (or any AFC value between 0.0 ppm and about 250 ppm, including endpoints 0.0 ppm and 250 ppm, in increments of 0.1 ppm, e.g., 4.1 ppm, or any range of AFC values between 0.0 ppm and about 250 ppm, including endpoints 0.0 ppm and 250 ppm, in increments of 0.1 ppm, e.g., from about 20.1 ppm to about 35.7 ppm).
76. The method of any one of embodiments 61 to 75, wherein the composition further comprises an available free chlorine (AFC) value of from greater than 0 ppm to about 100 ppm.
77. The method of any one of embodiments 61 to 76, wherein the composition has a pH of from about 1.5 to about 7.0 (or any pH between about 1.5 and about 7.0, including endpoints 1.5 and 7.0, in increments of 0.1, e.g., 2.7, or any range of pH between about 1.5 to about 7.0, including endpoints 1.5 and 7.0, in increments of 0.1, e.g., from about 2.4 to about 6.1 or from about 2.5 to about 4.0).
78. The method of any one of embodiments 61 to 77, wherein the composition has a pH of from about 2.0 to about 6.0.
79. The method of any one of embodiments 61 to 78, wherein the electrolyzed water has an oxidation reduction potential (ORP) value ranging from about +300 mv to about +1300 mv.
80. The method of any one of embodiments 61 to 79, wherein the electrolyzed water has an oxidation reduction potential (ORP) value ranging from about +500 mv to about +1150 mv.
81. The method of any one of embodiments 61 to 80, further comprising: adding one or more additional components to the ionized solution, the one or more additional components comprising one or more minerals, one or more vitamins, one or more medicines, or any combination thereof.
82. The method of embodiment 81, wherein the one or more medicines comprises potassium iodide.

83. The method of embodiment 81, wherein the one or more medicines comprises boric acid.
84. The method of embodiment 81, wherein the one or more medicines comprises iodoform.
85. The method of any one of embodiments 81 to 84, wherein each of the one or more additional components is present in an amount of greater than 0 wt % to about 3.0 wt %, based on a total weight of the composition (or any wt % between about 0.01 wt % and about 3.0 wt %, including endpoints 0.01 wt % and 3.0 wt %, in increments of 0.01 wt %, e.g., 0.1 wt %, or any range of wt % between about 0.01 wt % and 3.0 wt %, including endpoints 0.01 wt % and 3.0 wt %, in increments of 0.01 wt %, e.g., from about 0.01 wt % to about 0.03 wt %).
86. The method of any one of embodiments 61 to 85, wherein the composition is in the form of a liquid, gel, cream, or foam.
87. The method of any one of embodiments 61 to 25, wherein the composition is stable for at least 6 months.
88. The method of any one of embodiments 61 to 87, wherein the composition is stable for at least 1 year.

It should be understood that although the above-described compositions, and methods are described as "comprising" one or more components or steps, the above-described compositions, and methods may "comprise," "consists of," or "consist essentially of" any of the above-described components or steps of the compositions, and methods. Consequently, where the present invention, or a portion thereof, has been described with an open-ended term such as "comprising," it should be readily understood that (unless otherwise stated) the description of the present invention, or the portion thereof, should also be interpreted to describe the present invention, or a portion thereof, using the terms "consisting essentially of" or "consisting of" or variations thereof as discussed below.

As used herein, the terms "comprises," "comprising," "includes," "including," "has," "having," "contains", "containing," "characterized by" or any other variation thereof, are intended to encompass a non-exclusive inclusion, subject to any limitation explicitly indicated otherwise, of the recited components. For example, a composition and/or method that "comprises" a list of elements (e.g., components or steps) is not necessarily limited to only those elements (or components or steps), but may include other elements (or components or steps) not expressly listed or inherent to the composition and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a composition and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

Compositions as described in embodiments 1 to 28 were prepared. The compositions were applied onto surfaces such as the surface described in embodiments 29 to 33, and devices such as the surface described in embodiments 34 or 35.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A composition consisting of:
    electrolyzed water consisting of solubilized sodium chloride in deionized water and having an oxidation reduction potential (ORP) value ranging from about +100 mv to about +1600 mv;
    potassium alum or ionic components resulting from dissociated potassium alum within said electrolyzed water; and
    potassium iodide,
    wherein said composition (i) has a pH of from about 2.4 to about 6.1, and (ii) is useful as a disinfectant.
2. The composition of claim 1, wherein the potassium iodide is present in an amount of greater than 0 wt % to about 0.20 wt %, based on a total weight of the composition.
3. The composition of claim 2, wherein the potassium alum or ionic components resulting from dissociated potassium alum within said electrolyzed water is present in an amount of greater than 0 wt % to about 0.80 wt %, based on a total weight of the composition.

* * * * *